United States Patent
Peterson et al.

(12) 
(10) Patent No.: US 6,211,221 B1
(45) Date of Patent: Apr. 3, 2001

(54) DIETARY SUPPLEMENT CONTAINING HISTIDINE FOR ALLEVIATING DYSMENORRHEA, ENDOMETRIOSIS, AND PRE-TERM LABOR

(76) Inventors: Johnny W. Peterson, 3709 Pabst Rd., Dickinson, TX (US) 77539; Peter G. Thomas, 777 Tilmann Rd., Charlottesville, VA (US) 22901

( * ) Notice: Subject to any disclaimer, the term of this patent is extended or adjusted under 35 U.S.C. 154(b) by 0 days.

(21) Appl. No.: 09/285,717

(22) Filed: Apr. 5, 1999

(51) Int. Cl.⁷ .................................................. A61K 31/415
(52) U.S. Cl. ........................ 514/399; 514/400; 514/899
(58) Field of Search .................... 514/399, 400, 514/899

(56) References Cited

U.S. PATENT DOCUMENTS

| | | | |
|---|---|---|---|
| 5,352,691 | * 10/1994 | Thomas | 514/385 |
| 5,741,807 | * 4/1998 | Thomas | 514/399 |
| 5,811,446 | * 9/1998 | Thomas | 514/399 |
| 5,925,619 | * 7/1999 | Walsh et al. | 514/15 |
| 5,972,985 | * 10/1999 | Thomas et al. | 514/400 |

FOREIGN PATENT DOCUMENTS

0652012 A1 * 5/1995 (EP).

* cited by examiner

*Primary Examiner*—Kevin E. Weddington
(74) *Attorney, Agent, or Firm*—Isaac Angres; Susan Petraglia

(57) ABSTRACT

The present invention relates to methods for alleviating disorders or chronic conditions of the female reproductive system, such as dysmenorrhea, endometrial pain, and pre-term labor, through dietary supplementation with histidine. The invention relates further to novel combination supplements of histidine in conjunction with other nutritional supplement materials which are preferably also useful in alleviating the above-mentioned disorders or conditions. A method for administering a dietary histidine supplement in conjunction with one or more separately formulated therapeutic drugs also known to be useful in treating these female reproductive conditions is also disclosed.

26 Claims, 8 Drawing Sheets

PGE$_2$-IMIDAZOLE ADDUCT

FIG. 5

*Key:
s = singlet
br = broad
dd = doublet of doublets
t = triplet
q = quartet
m = multiplet TABLE 1: $^1$H NMR Assignments for $PGE_2$ – Imidazole Complex

| Atom # | δ (ppm) (chemical shift) | Integral/multiplicity *key |
|---|---|---|
| IMD H2 | 8.81 | 1H/s |
| IMD H4 | 7.46 | 1H/s |
| IMD H5 | 7.62 | 1H/s |
| H2 | 2.29 | 2H/t |
| H3 | 1.57 | 2H/m |
| H4 | 1.99 | 2H/br q |
| H5 | 5.45 | 1H/br q |
| H6 | 5.32 | 1H/br q |
| H7 | 2.36 | 2H/br t |
| H8 | 2.58 | 1H/m |
| H10 | 3.07 | 1H/dd |
| H10 | 2.79 | 1H/br dd |
| H11 | 4.84 | 1H/br q |
| H12 | 2.9 | 1H/br q |
| H13 | 5.55 | 1H/dd |
| H14 | 5.37 | 1H/dd |
| H15 | 4.03 | 1H/br q |
| H16 | 1.39 | 1H/m |
| H16 | 1.29 | 1H/m |
| H17 | 1.16 1.08 | 2H/m |
| H18 | 1.08 | 2H/m |
| H19 | 1.16 | 2H/m |
| CH3-20 | 0.76 | 3H/br t |

DIETARY SUPPLEMENT CONTAINING HISTIDINE FOR ALLEVIATING DYSMENORRHEA, ENDOMETRIOSIS, AND PRE-TERM LABOR

FIELD OF THE INVENTION

The present invention relates to methods and compositions for alleviating conditions or disorders of the reproductive system of a woman, by administering a daily supplement of histidine alone or in combination wit drugs or other nutritional supplements. The invention relates also to novel dietary supplements.

BACKGROUND OF THE INVENTION

Dysmenorrhea is a common repetitive disorder affecting female adolescents and women, and is closely associated with the menstrual cycle. Over the years, there has been a widespread mischaracterization of dysmenorrhea as simply a painful menstruation or menstrual cramping. There are several types of dysmenorrhea, as defined for example in Taber's Cyclopedic Medical Dictionary ($12^{th}$ edition). However, the two types that are most prevalent and most prevalently studied are primary dysmenorrhea and secondary dysmenorrhea. In primary dysmenorrhea there is no underlying or associated organic pathology of either the uterus, fallopian tubes, or ovaries. Where an organic pathology of the type just mentioned does exist, the resulting dysmenorrhea is termed secondary. Some causes of secondary dysmenorrhea are endometriosis, uterine myomas (and polyps and adhesions), ovarian cysts, adenomyosis, pelvic inflammatory disease (PID), and the presence of an intrauterine device. For a thorough modern day treatment of the etiologic bases of dysmennorrhea and premenstrual syndrome, including studies and a historical perspective of therapy regimens, see, for example, Dawood M.D., M. Y. et al, *"Premenstrual Syndrome and Dysmenorrhea"*, (Urban & Schwarzenberg 1985) incorporated herein in pertinent part by reference.

While primary and secondary dysmenorrheas require different management or therapy (the latter type usually requiring surgery), both types involve increased levels of prostaglandin synthesis. The increased prostaglandin synthesis results from the loss of hormonal support at menses (i.e., low progesterone), which triggers the release of arachidonic acid from phospholipids under the action of phospholipase $A_2$. Arachidonic acid is the essential starting material for prostaglandin biosynthesis, in the presence of the enzyme cyclooxygenase. Prostaglandins are smooth muscle-stimulating agents, hence giving rise to increased uterine contractility. The major prostaglandins involved in uterine function are $PGE_2$, $PGF_{2\alpha}$, and $PGI_2$ (prostacyclin). The key role of prostaglandins in dysmenorrhea was first noted in 1957 by Pickles, who observed their presence in menstrual fluid. Pickles later identified the principle component of the prostaglandins as a mixture of $PGF_{2\alpha}$ and $PGE_2$. Another researcher by the name of von Euler pin-pointed $PGF_{2\alpha}$ (also known as "prostaglandin $F_{2\alpha}$") as the agent responsible for stimulating the normal expulsive contractions of the myometrium. Hence, the symptomology of dysmenorrhea resembles that of the side effects of prostaglandin administration. Namely, nausea, vomiting, diarrhea, vasoconstriction (i.e., uterine ischemia), and severe uterine cramps. Irritability and other psychological disturbances are also symptoms of dysmenorrhea. The physical pain of dysmenorrheic uterine cramping or hypercontractility is directly the result of increased production of prostaglandin $F_{2\alpha}$ either before or with onset of menstruation.

The modalities for managing or treating primary dysmenorrhea are different from those for managing or treating secondary dysmenorrhea. This is due in large part to the fact that the latter almost always ultimately requires a surgical intervention (oftentimes preceded by an unsuccessful attempt at drug therapy), whereas the former can be effectively brought under control by administering drug therapy.

The chief therapies for primary dysmenorrhea are administration of oral contraceptives (endocrine therapy) and prostaglandin synthetase inhibitors. Essentially all non-steroidal antiinflammatory agents (NSAIDS) fall into the latter group. Oral contraceptives are the ideal choice for treating a dysmenorrheic woman where that woman's primary objective is birth control. Birth control pills are believed to reduce prostaglandin levels in menstrual fluid by 1) reducing the volume of menstrual fluid by suppression of endometrial tissue growth, and 2) by inhibiting ovulation, thereby creating an endocrine milieu wherein prostaglandins are low and luteal phase progesterone levels, believed to be necessary for prostaglandin biosynthesis, are absent. However, oral contraceptives are not the primary choice of birth control for all women of child-bearing years for a number of reasons. For example, birth control pills carry numerous contraindications, and they must be taken regularly at least three (sometimes four) weeks of the month.

Prostaglandin synthetase inhibitors (PSIs), on the other hand, are given typically 2–3 days of the menstrual cycle for treating primary dysmenorrhea. There are two types of PSIs. Type I prostaglandin synthetase inhibitors are those that inhibit the enzyme cyclo-oxygenase, thereby blocking the conversion of arachidonic acid to cyclic endoperoxides. Type II prostaglandin synthetase inhibitors are those that inhibit the isomerase and reductase enzymes, thereby preventing the conversion of endoperoxide to prostaglandin. NSAIDS that are type I PSIs include aspirin, indomethacin, meclofenamic acid, and ibuprofen. NSAIDS that are type II PSIs include phenylbutazone and p-chloromercuribenzoate. A large number of compounds fall under the umbrella of NSAIDS and all demonstrate, in varying degrees, the ability to inhibit prostaglandin synethesis. These include aryl carboxylic and arylalkanoic acids, acetic acid analogs, propionic acid analogs, fenamates, and enolic acids (including pyrazolidinediones). While NSAIDS are predominantly the treatment of choice for primary dysmenorrhea over oral contraceptives, NSAIDS are not without side effects. The predominant side effects are various gastrointestinal disorders (e.g., gastric ulceration), renal dysfunction, and disturbances of the central nervous system (e.g., headache, dizziness, and drowsiness).

Other drug-related therapies for dysmenorrhea include progesterone-medicated intrauterine devices, and calcium antagonists (to inhibit muscle contraction). Limited efficacy has been observed with administration of betamimetic agents, and tocolytic agents (i.e., ethanol).

The management of secondary dysmenorrhea generally entails elucidating the underlying organic pathology and correcting it usually with surgery. Any medicinal therapy administered to a woman with secondary dysmenorrhea is an interim measure to bring some relief of symptoms while the underlying pathology is elucidated and/or the patient awaits appropriate surgery. However, there are certain instances of secondary dysmenorrhea where a medicinal management is appropriate. For example, women who develop dysmenorrhea from the use of an IUD should be prescribed an effective prostaglandin synthetase inhibitor. Also, hormone therapies, e.g., with danazol and certain gonadotropin releasing hormone analogues, have been effective in relieving the dysmenorrhea and pelvic pain caused by endometriosis. Combination therapy of danazol in conjunction with oral contraceptives has been shown not only to relieve the pain associated with endometriosis, but also to cause a regression of the disorder.

Admittedly, great strides have been made in the past forty years in the understanding of the nature and types of dysmenorrhea, as well as in how to manage or treat this disorder that affects most, if not all, of adolescent females and women. While the benefits offered by the highly efficacious prostaglandin synthetase inhibitors (NSAIDS) seem to outweigh their side effects, and the same could possibly be said for oral contraceptive therapy, there is still a need in the art for the discovery of other regimens of equal or greater efficacy to NSAIDS, while having far fewer contraindications for the management of dysmenorrhea, endometriosis, and pre-term labor.

Carnouvis, C. P. et al, *Am. J. Physiol.,* 255, F685-9 (1988) and Burch, R. M. et al, *J. Pharmacol. Exp. Ther.,* 210, 344-8 (1979) have demonstrated in in vitro studies with toad urinary bladder preparations that histidine decreased $PGE_2$ synthesis therein. Steinhauer, H. B. et al, *Clin. Nephrol.,* 24, 63–68 (1985) report that histidine diminishes $PGE_2$ and thromboxane $B_2$ levels in spontaneous murine autoimmune disease. Also, Steinhauer, H. B. et al, *Prostaglandins Leukotrienes Med.,* 13, 211–16 (1984).

However, as yet unrecognized or suggested in the art, the present invention is based on the discovery that the amino acid histidine is both effective and highly safe in alleviating a number of reproductive disorders, and/or at least certain symptoms thereof, in the human female and in other women.

SUMMARY OF THE INVENTION

The present invention is based on the discovery that histidine, when administered in the form of a daily dietary supplement or a medical food to a human female is useful in alleviating or averting the severity of prostaglandin-related disorders of the female reproductive system. For example, one object of the invention is a method for alleviating the physical and/or psychological discomfort associated with primary dysmenorrhea by supplementing the diet of a female subject with an effective daily supplement of histidine.

Another object of the invention is a method for alleviating certain types of secondary dysmenorrhea. In this regard, the method comprises alleviating the severity of endometriosis in a female subject by supplementing her diet with an effective daily supplement of histidine. Also within the context of alleviating secondary dysmenorrhea, the invention also embodies, for example, methods for alleviating secondary dysmenorrhea arising in a human female as the result of intrauterine device use, ovarian cysts, polycystic ovary syndrome, or a number of other disorders of the female reproductive system.

Yet still another object of this invention is a method for either decreasing the likelihood of onset of pre-term labor in a pregnant female, or alleviating a pre-term labor, by supplementing the diet of the pregnant female with an effective daily supplement of histidine, so that the pre-term labor either does not occur or is alleviated sufficiently to extend the pregnancy to as close to full term as possible.

The invention also embodies novel dietary supplement or medical food compositions containing histidine in combination with one or more additional dietary/nutritional supplements which are also useful in moderating any of the above-described female reproductive disorders.

These and other objects will be further understood and appreciated from the following detailed description of the invention, the examples, and the appended claims.

BRIEF DESCRIPTION OF THE FIGURES

FIG. 5 is a table of proton NMR assignments for $PGE_2$-imidazole complex.

DETAILED DESCRIPTION OF THE INVENTION

Figure 1:
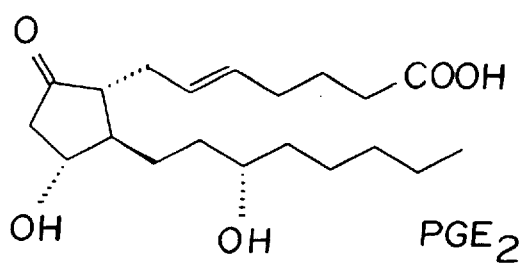
FIG. 1 depicts the reaction scheme between prostaglandin $PGE_2$ and the imidazole moiety of histidine.
Figure 1:
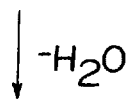
Figure 1:
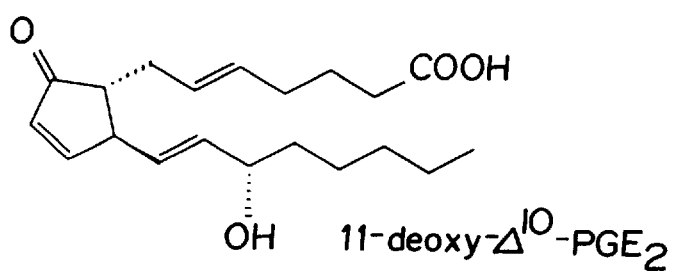
Figure 1:
Figure 1:
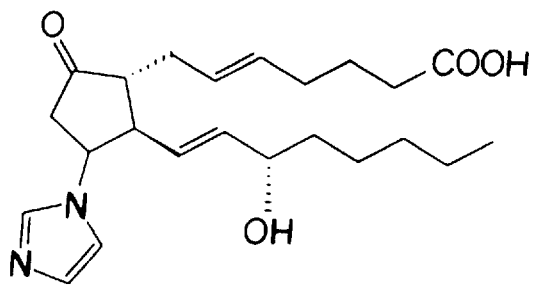

The present invention provides effective and highly safe methodologies for alleviating prostaglandin-mediated disorders of the human female reproductive system, by administering an effective daily dietary supplement containing histidine. More particularly, prostaglandins play a central role, for example, in primary dysmenorrhea (frequently given the short-hand abbreviation "menstrual cramping"), secondary dysmenorrhea, in the pain associated with endometriosis, in pre-term or premature labor, and in other instances of uterine hypercontractility and ischemia. The terms "human female" or "female subject" mean both women of child-bearing years and post-menopausal women using hormone replacement therapy. In certain embodiments, the woman subject is an insulin-resistant woman.

The methodologies herein described are for alleviating the symptoms of certain female reproductive disorders in which prostaglandins are involved. By "alleviating" is meant the ability to curtail one or more symptoms of the enumerated disorders. Alternatively, "alleviating" as used throughout the disclosure may also mean the ability to curtail the onset of the chemical chain of events that lead to the manifested symptoms, e.g., by inhibiting prostaglandin synthesis or inactivating prostaglandin molecules before expression of the cascade of sequelae. Terms such as "averting", "moderating", "abating", or "relieving" are intended to be interchangeable with "alleviating".

One of the present embodiments is a method for alleviating one or more sequela of dysmenorrhea in a human female by administering to the female subject at a time prior to menses, and continuing for the duration of menses, a daily supplement of histidine that is effective to alleviate, moderate, or abate one or more sequelae thereof. As will be described in greater detail below, the supplement of histidine is administered in conjunction with at least one pharmacologically acceptable carrier. The chief manifestations, or sequelae, of dysmenorrhea are nausea, vomiting, diarrhea, vasoconstriction, i.e., uterine ischemia, and (which leads to) severe uterine cramping. Irritability and other psychological disturbances are also sequelae of dysmenorrhea and can be abated by dietary histidine. Both primary and secondary dysmenorrheas fall within the methods of the present invention. Cramps associated with pre-menstruation and/or menses are a symptom of primary dysmenorrhea and can be alleviated or moderated preferably by adding histidine to the woman's diet prior to onset of menstruation (e.g., one to two weeks prior), with continued administration for as many days, of menses that the menstrual cramps persist. Moreover, since histidine is a compound that is both safe and well-tolerated by the body at high doses, a female subject could also take a histidine supplement daily for the entire monthly cycle.

The secondary dysmenorrheas that can be relieved within the context of the invention have an underlying pathologic origin. These include endometriosis, pelvic inflammation, pelvic infection, adenomyosis, uterine myoma, uterine polyps, uterine adhesions, congenital malformations of the Mullerian system, cervical stenosis, ovarian cysts, pelvic congestion syndrome, polycystic ovary syndrome(PCOS), and Allen-Master's syndrome. In certain of these underlying pathologies the secondary dysmenorrhea is a sequela thereof, and in others the dysmenorrhea results from treating the underlying condition, e.g., as in PCOS (which is a major cause of infertility, especially in insulin-resistant women). Alleviating or moderating secondary dysmennorrhea that arises in a woman from the presence of a contraceptive intrauterine device(IUD) or any other IUD is also a part of the present embodiment.

For this embodiment and all others to now be described, "histidine" encompasses either enantiomer, a racemic mixture, non-racemic mixtures, the free base form of histidine, and pharmacologically acceptable salts that can be reduced to L- or D-histidine. These histidine compounds are readily commercially available from numerous suppliers and/or manufacturers of nutritional supplements and from pharmaceutical suppliers. Where it is useful in the practice of the invention to employ a mixture of D- and L- histidine that is enriched in one enantiomer, such a mixture can be prepared by physically admixing the desired quantity of each of the enantiomers. Histidine derivatives and analogs which are recognized in the art as being suitable for nutritional are also intended for use in the present embodiments. More preferably, the histidine compound is L-histidine or a pharmaceutically acceptable salt of L-histidine.

The administration of histidine according to another embodiment of the invention is useful in alleviating pelvic pain in women suffering from endometriosis. The typical "cure" for endometriosis is surgical oophorectomy, the most effective way to eliminate the ovarian sex steroid production, which is the cause of endometriosis. However, histidine administration as a dietary supplement or in the form of a medical food is a way to alleviate the secondary dysmenorrhea arising as a consequence of endometriosis.

However, surgical intervention will be the primary treatment for endometriosis and for many other underlying organic pathologies causing a secondary dysmenorrhea. Prostaglandins are formed rapidly in damaged tissue. The tissue at and around the excision locus will be damaged or traumatized surgically, thereby raising the levels of prostaglandins and prostaglandin side effects in that area. Therefore, among the present embodiments is a method for inactivating prostaglandins formed during oophorectomy or any other surgical procedure to correct an underlying pathology of a secondary dysmenorrhea, by supplementing the diet of the female patient with histidine before and after the surgical procedure.

Another embodiment of the invention is the use of a histidine dietary supplement for diminishing the likelihood of onset of pre-term labor in a pregnant woman or other pregnant mammal. These objectives are accomplished by supplementing the diet of a pregnant woman or other pregnant mammal with an amount of D-histidine, L-histidine, a therapeutically acceptable salt of histidine which can be reduced to D- or L-histidine, or mixtures thereof, that is effective to prevent, or control the pre-term labor by extending it to substantially a full-term. Histidine as a dietary supplement or in the form of a medical food can be administered most efficaciously via oral formulations. However, intravenous formulations may also be appropriate depending on the circumstances of the female subject. It is anticipated that the use of the present histidine supplements, containing larger, more efficacious amounts of histidine, will obviate the need for using conventional pre-term labor therapeutics, e.g., Sulindac(clinoril), that carry the risk of side effects on mother and unborn child. At the very least, it is contemplated herein that a histidine dietary supplement could be co-administered with other pre-term labor therapeutics such that the latter (the drug) could be given in a reduced amount.

As stated previously in the Background of the Invention, certain therapeutic agents for prostaglandin-mediated conditions act at the level of inhibiting prostaglandin synthesis (i.e., prostaglandin synthetase inhibitors). While not wishing to be bound by any one particular theory for the underlying mode of action, the effectiveness of histidine administration is believed to be due to the inactivation of prostaglandins formed, rather than inhibition of prostaglandin synthesis. More specifically, unpublished studies of one of the present co-inventors reveal that L-histidine chemically reacts with $PGE_2$ thereby disabling or inactivating the prostaglandin in its role in the inflammatory cascade (e.g., $PGE_2$'s stimulatory effect on adenylate cyclase). The chemical transformation of $PGE_2$ with imidazole is shown in FIG. 1 and is thought to proceed by an initial dehydration of the prostaglandin molecule to yield the alpha, beta- unsaturated ketone 11-deoxy-$\Delta^{10}$-$PGE_2$. The dehydration is thought to be acid/base catalyzed by imidazole, or by the imidazolyl ring of L-histidine or histidine analogs. For example, addition of imidazole by Michael-addition to the alpha, beta-unsaturated ketone yields the 11-deoxy-11-imidazolyl-$PGE_2$. The NMR spectrum (FIG. 2) and mass spectra (FIGS. 3A and 3B) confirm that the product of the reaction mechanism shown in FIG. 1, $PGE_2$-imidazole, is formed. A similar covalent bond is formed between $PGE_2$ and L-histidine.

Mass Spectrometry analysis of the $PGE_2$-imidazole complex. FAB-MS analyses of the $PGE_2$-imidazole complex isolated from either HPLC peak (FIG. 3—peak 1 or peak 2) showed an intense $(M+H)^+$pseudomolecular ion at m/z 403. Similar data were obtained with ESI-MS. The presence of a single imidazole moiety in the complex was confirmed by analysis of a U-[$^{15}$N]-imidazole product, which gave an intense pseudomolecular ion at m/z 405. The presence of a free carboxylic acid was indicated by successful esterification of the $PGE_2$-imidazole complex. This was demonstrated by the FAB-MS spectrum of the product which showed a $(M+H)^+$pseudomolecular ion at m/z 419 (methanol) and m/z 422 ($d_3$-methanol). Analysis of the acetylated complex (U-[$^{15}$N]-labeled) by ESI-MS showed an $(M+H)^+$at m/z 489 consistent with the reaction of two acetyl groups.

Figure 2A:
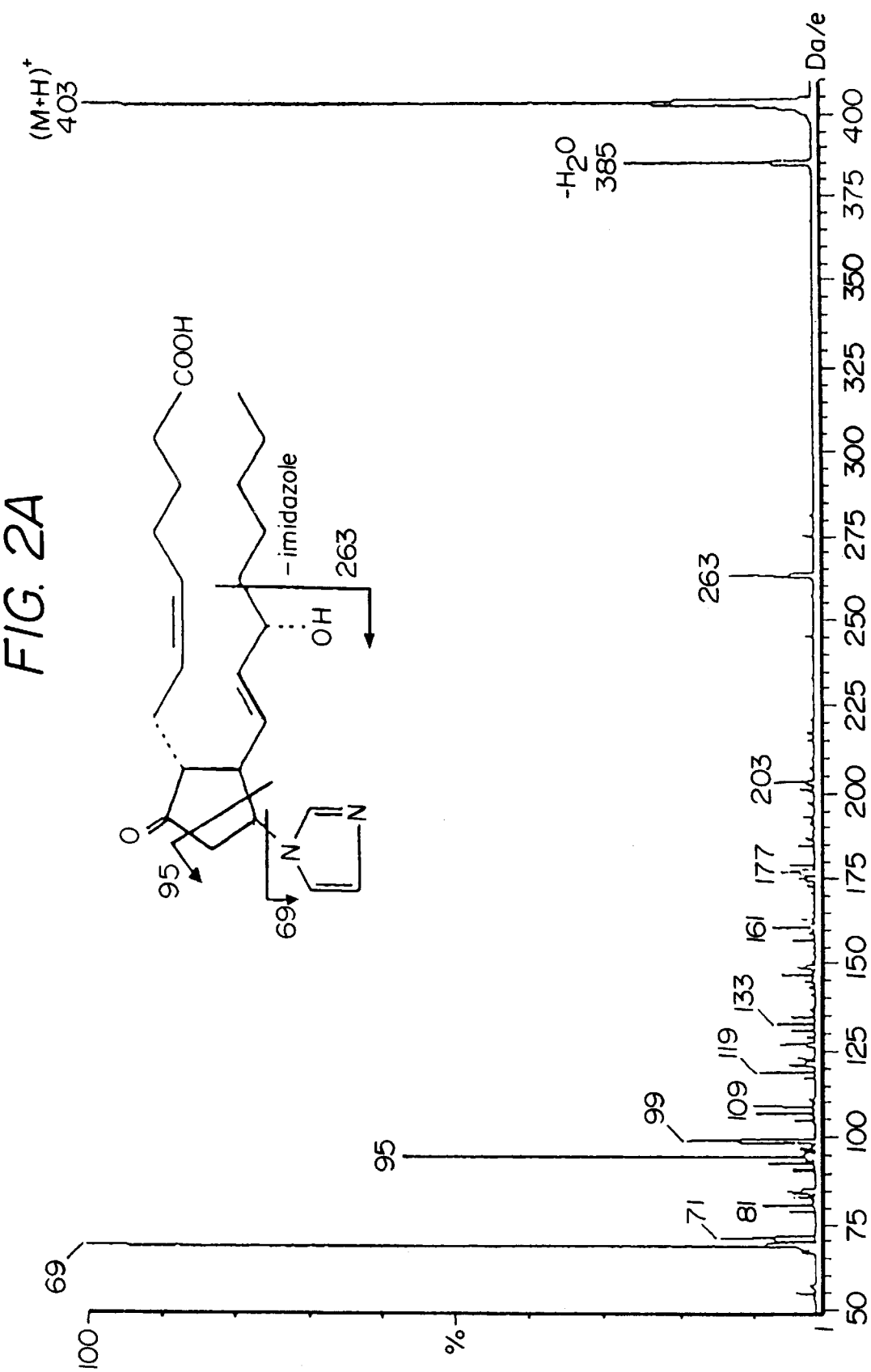
FIGS. 2A and 2B are mass spectral analyses for $PGE_2$-imidazole.
Figure 2B:
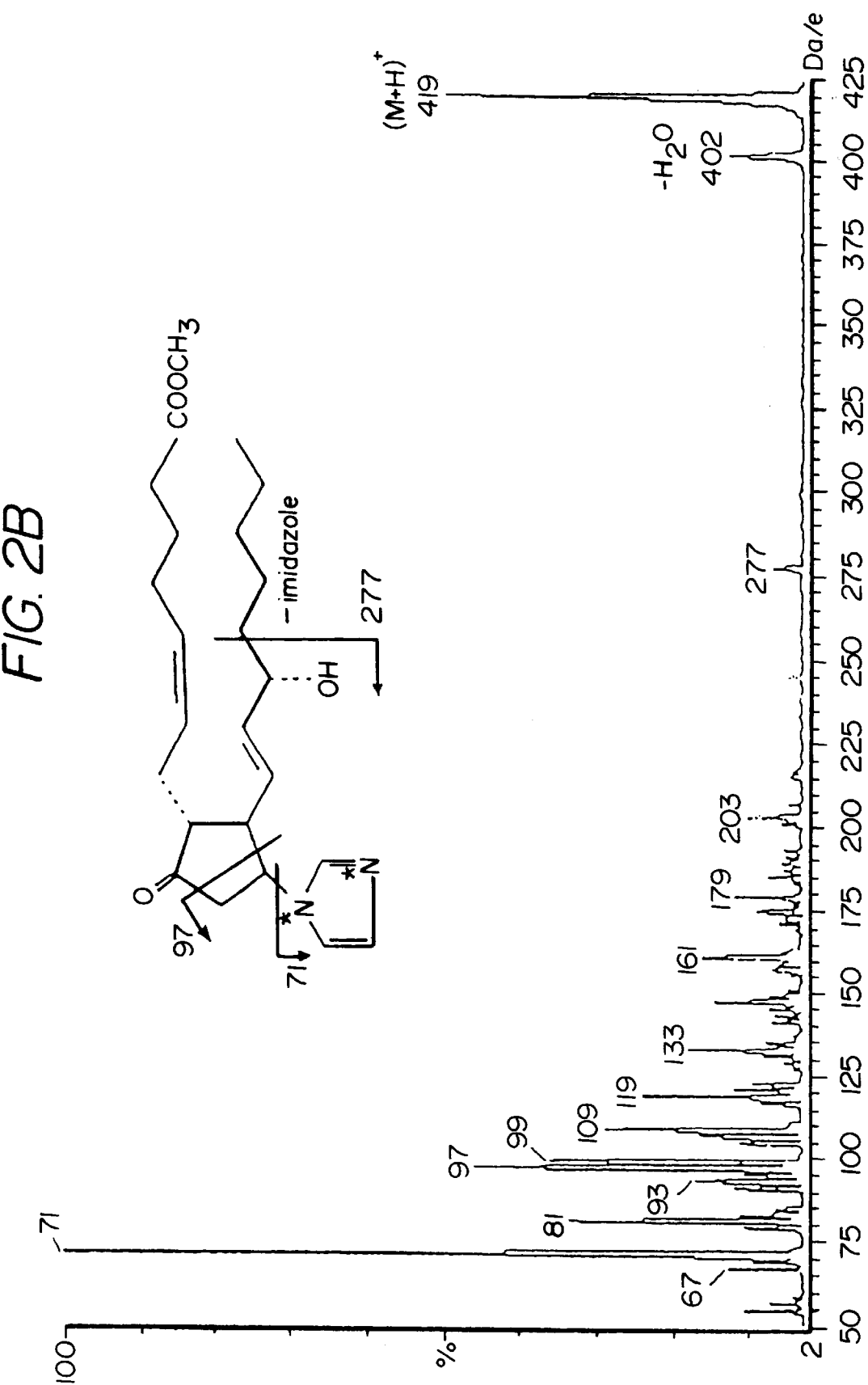
Figure 3:
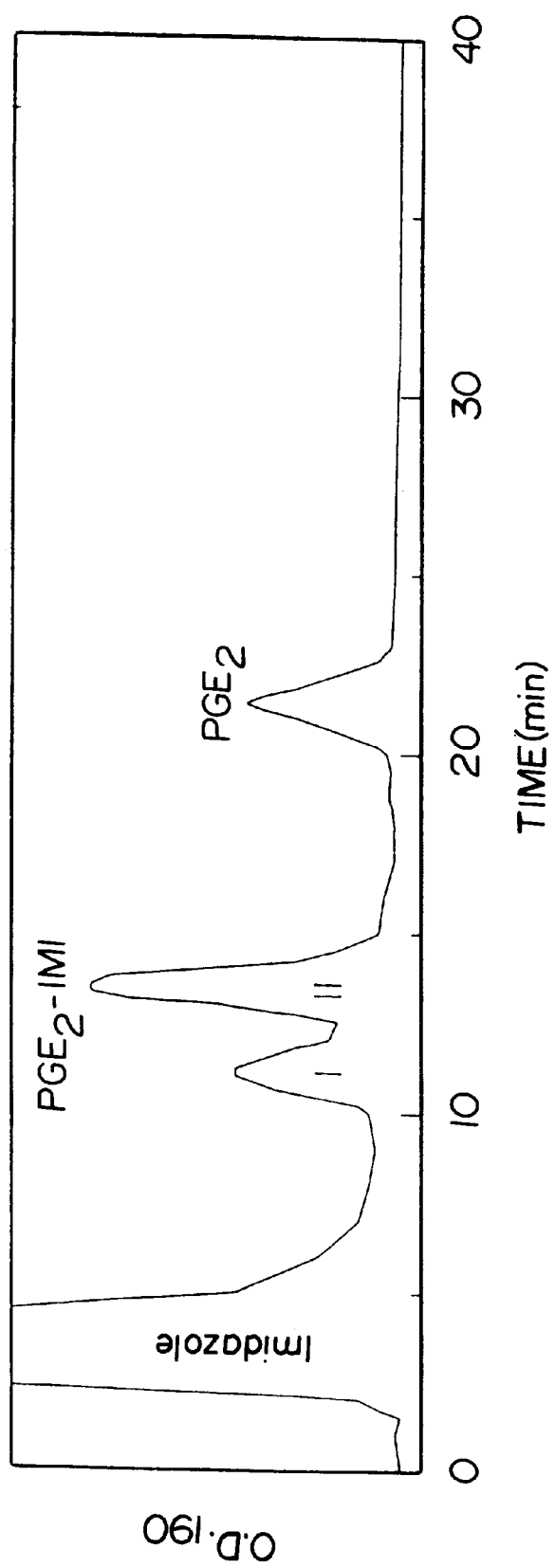
FIG. 3 is a C-18 reverse-phase chromatogram of $PGE_2$-imidazole complex obtained at 190 nm.

Collisionally-induced dissociation (CID) of the $PGE_2$-imidazole complex and a number of derivatives was also performed (following methods outlined in Zirrolli, J. A. et al, *J. Am. Soc. Mass Spectrom,* 1, 325–335 (1990)). The spectrum obtained for the $PGE_2$-imidazole complex is illustrated in FIG. 2A. The major daughter ions at m/z 69 and 95 can be assigned to fragmentation of the imidazole moiety and this was confirmed by the corresponding daughter ion spectra of the U-[$^{15}$N]-labeled complex, which showed similar intense daughter ions at m/z 71 and 97. The signal at m/z 263, which was retained in the spectrum of the U-[$^{15}$N]- complex, was consistent with a concerted fragmentation mechanism involving elimination of the imidazole and cleavage at C15. Elimination of water from the molecular ion accounted for the signal m/z 385, whereas the low intensity ions between m/z 100–200 were consistent with cleavage along the methylene chains. FIG. 2B illustrates the ESI-MS/MS daughter ion spectrum for the esterified $PGE_2$-imidazole complex and lends support to the ion assignments already given.

Figure 4A:
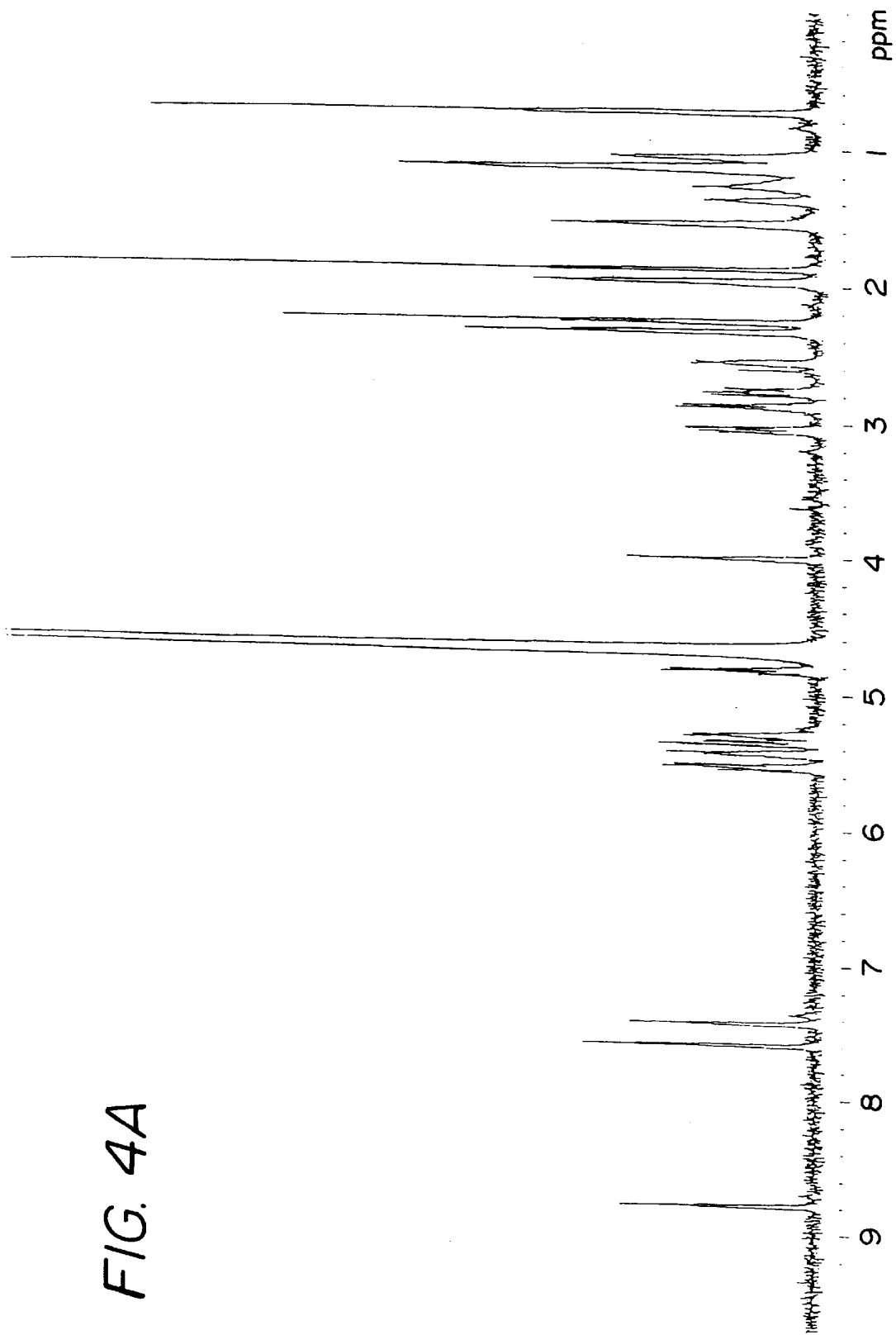
FIGS. 4A–C are the NMR spectra of the reaction product of $PGE_2$ and imidazole.
Figure 4B:
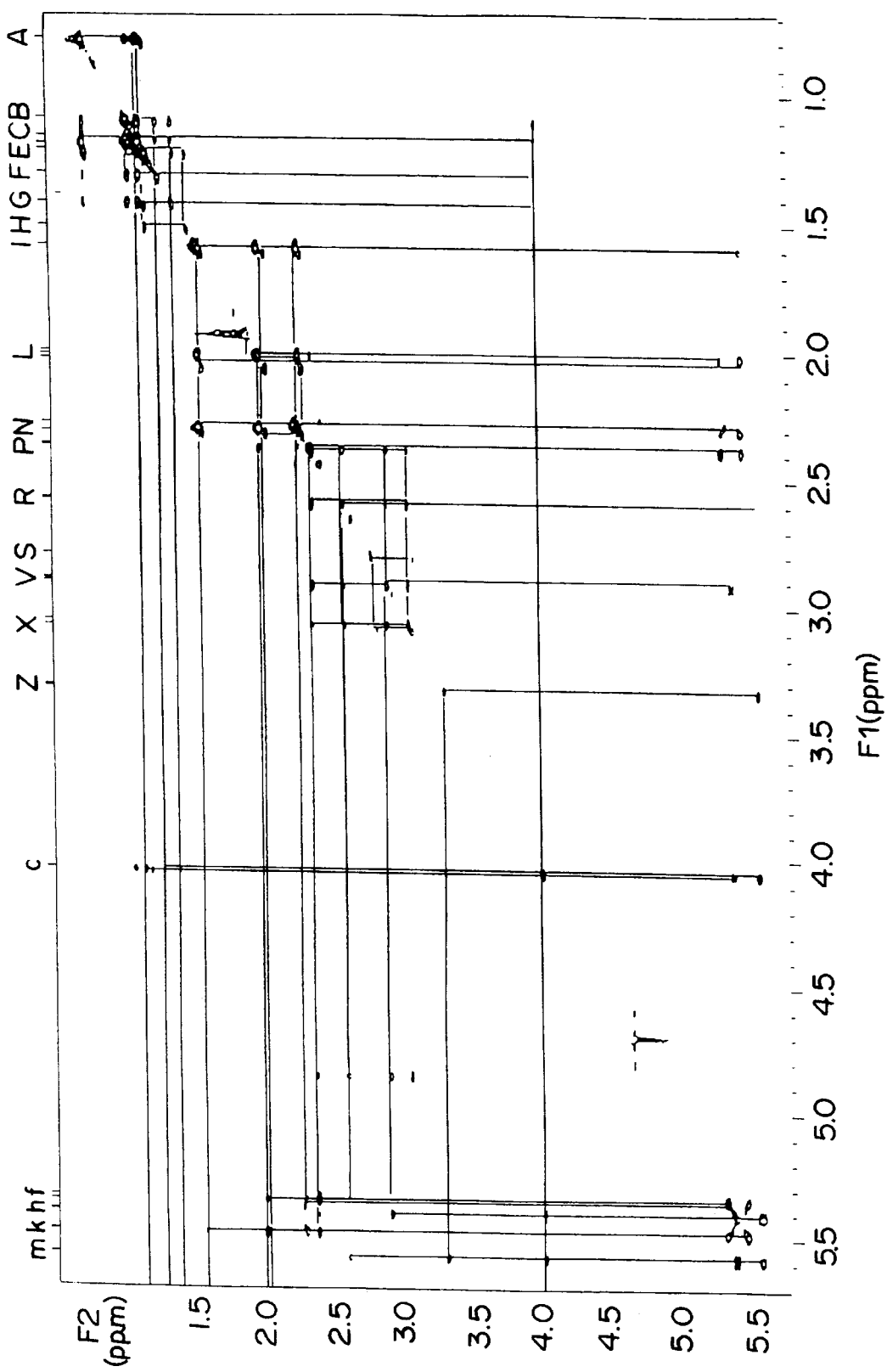
Figure 4C:
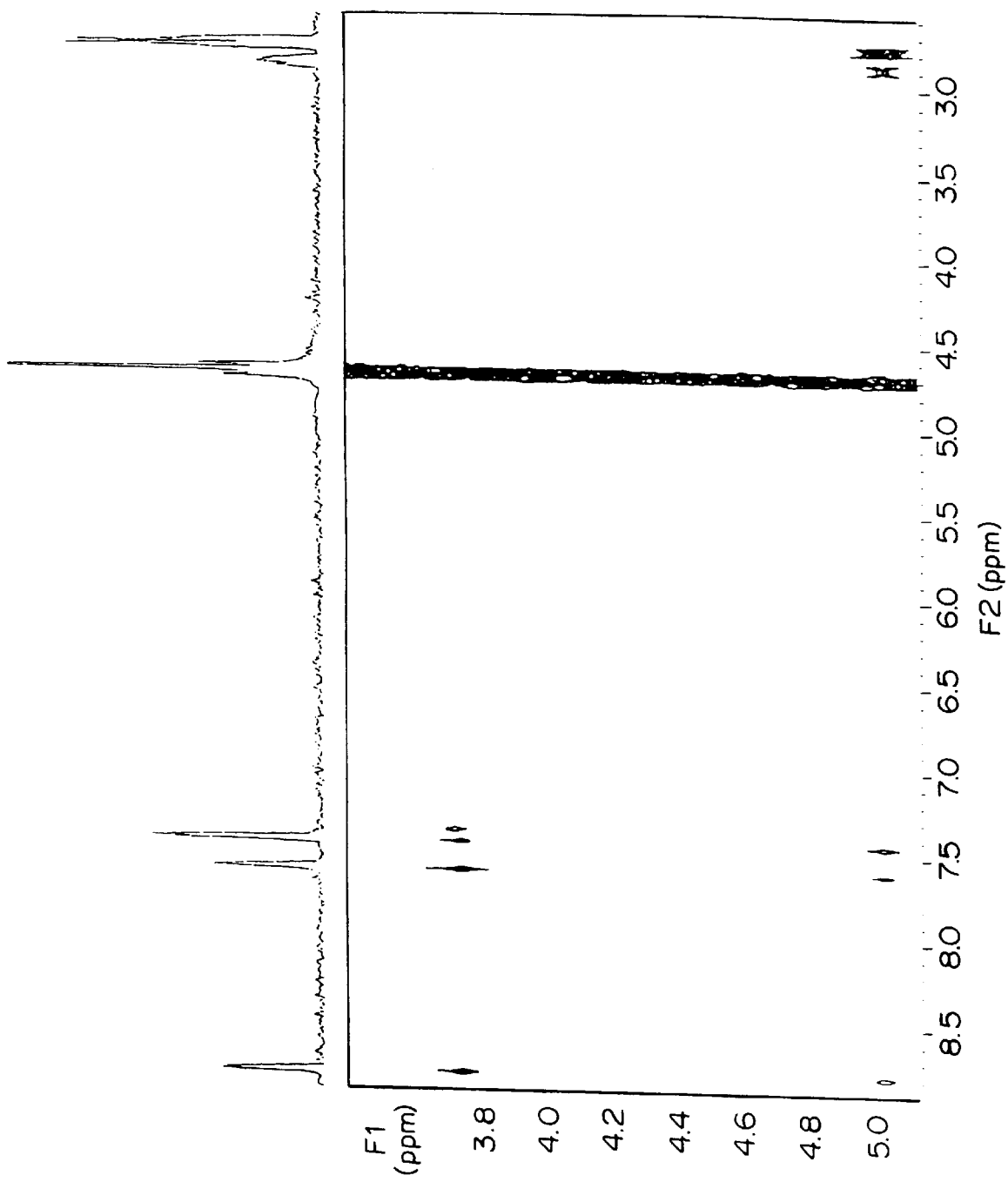

Derivation of the structure of the $PGE_2$-imidazole complex by NMR. Specific information about the chemical structure of $PGE_2$-imidazole was derived from NMR analysis and fragmentation patterns by mass spectrometry. The 1D $^1H$ NMR spectrum of the $PGE_2$-imidazole complex is shown in FIG. 4. The assignments of the $^1H$ signals was accomplished through analysis of the 2D COSY and TOCSY spectra (FIG. 4B). During the course of the 2D NMR spectra acquisition, some degradation of the sample was noted with several new peaks appearing. The assignments were straightforward, with crosspeaks in the TOCSY spectra connecting many of the coupled protons. Thus, TOCSY correlation is seen for H-13 (5.55 ppm) to 14, H-15 and H-12 (in order of crosspeak appearance; see FIG. 1 and FIG. 5 for identification of protons). H-5 (5.45 ppm) shows correlation to H-7, H-2, H-4, and H-3. H-14 (5.37 ppm) is correlated to H-13, H-15, and H-12. H-6 (5.32 ppm) is correlated to H-5, H-7, H-2 and H-4. H-11 (4.84 ppm) shows correlation in the dimension F-2 to H-10, H-12, H-8 and H-7 (water presaturation obscures the diagonal peak and correlation in the F1 dimension). H-15 (4.03 ppm) is correlated to H-13, H-14, H-15, H-16, H-16', H-17 and H-17'. H-10 (3.07 ppm) is correlated to H-11, H-12, H-8 and H-7. Continuing upfield, H-12, H-8, H-7, H-2, H-4 and H-3 show the expected crosspeaks. Finally H-19 (1.16 ppm), H-18 (1.08 ppm) and H-20 (0.76 ppm) show correlation to each other as well as H-15 and H-16, thus completing the sequential connectivity of the protons of the prostaglandin adduct. The downfield imidazole ring protons were assigned through the COSY and TOCSY spectra, as well as the $^{15}N/^1H$ HMBC spectrum of the U-$^{15}N$-labeled imidazole $PGE_2$-imidazole complex sample (FIG. 4C). The latter spectrum correlated the $^{15}N/^1H$ coupled imidazole nitrogens with the imidazole protons H-2, H-4 and H-5 as well as two of the prostaglandin protons. Thus, N-1 of the imidazole (5.02 ppm) shows correlation to imidazole H-2 (8.81 ppm), H-4 (7.46 ppm), and H5 (7.62 ppm) as well as prostaglandin protons H-12 (2.90 ppm) and H-10[1] (2.79 ppm). Unfortunately, either because of small coupling or partial signal saturation due to the proximate HDO resonance, only a small, tentatively identified cross peak to the H-11 proton was observed. The correlation to both H-10 and H-12 (large three-bond coupling) confirms the site of covalent attachment of the imidazole ring to the prostaglandin framework. In addition the only significant chemical shift perturbations in the complex relative to those of the free $PGE_2$ is found for H-11 (+0.74 ppm; + values represent downfield shift for the complex), H-10, 10 (+0.65 and +0.35 ppm), H-12 (+0.47 ppm), H-8 (0.27 ppm) and H-14 (−0.19 ppm).

Because histidine is a naturally occurring amino acid, it is well-tolerated at high doses without attendant toxicities and side effects. In general, an effective amount of histidine in the context of the invention is from about 500 mg to 30 g daily for human applications. Where the present embodiments are applicable to larger mammals, e.g., in veterinary applications for pre-term labor, the upper limit may be greater and readily determined by the treating physician considering the age and weight of the patient and the severity of the condition.

Compositions and methods for the coadministration of histidine with other nutritional agents or supplements form a part of the present invention. In methods of coadministering histidine with one or more nutritional or dietary supplements it is envisioned that all of the nutritional materials can be administered either simultaneously or sequentially. Preferably, the effective daily supplement of histidine may be co-formulated with the additional dietary supplements in a single composition. Alternatively, where sequential co-administration is more appropriate or practical, then separate dosage forms for administration by the same or different route of administration will be used.

In those instances where it is advantageous to co-administer histidine with one or more additional known supplements, the dose of the additional supplement is typically a recommended daily allowance as disclosed, e.g., in *Drug—Facts and Comparisons* (1997 Edition) and incorporated herein by reference.

Additional supplements that may be co-formulated or co-administered with a dietary supplementing amount of histidine include vitamins, minerals, electrolytes, other amino acids, carbohydrates, protein substrates(e.g., crystalline amino acid infusions) and combinations of these, so long as the combination exhibits the desired effect of alleviating or moderating the conditions specified herein. The additional supplements may be in oral form, intravenous form, or enteral form. More particularly, the additional supplements may be any of those disclosed, for example, in *Drug—Facts and Comparisons* (1997 Edition) under the heading of "Nutritional Products", the entire contents of which are incorporated herein by reference.

Preferably, a dietary supplementing amount of histidine is combined with a mineral/electrolyte such as magnesium (which has known tocolytic activity for pre-term labor), preferably in pharmaceutically acceptable salt form, calcium, preferably in pharmaceutically acceptable salt form, or other pharmacologically recognized administerable forms of these minerals given their respective solubilities in an aqueous environment. More preferred for combination with a histidine dietary supplement is magnesium sulfate, calcium gluconate, calcium glubionate, calcium gluceptate, calcium lactate, calcium acetate, tricalcium phosphate, calcium glycerophosphate, or calcium carbonate in an amount that is nutritionally beneficial. A "nutritionally beneficial" amount is one that is readily understood by a nutritionist of ordinary skill in the art and, e.g., as disclosed in *Drug— Facts and Comparisons* and *The Physicians GenRx—Drug Information*, the relevant portions of which are incorporated herein by reference. Also, when a combination supplement is appropriate, it is understood that the additional supplement may require a route of administration different from that used for histidine (e.g., most calcium supplements are recommended for IV or intramuscular delivery).

Histidine in accordance with the invention is formulated in conjunction with at least a pharmaceutically acceptable carrier. There are numerous and diverse types of acceptable carriers which are readily appreciated by those skilled in the art depending on the route of histidine administration. The routes of histidine administration that are appropriate in the practice of the invention include oral, intravenous (I.V.), enteral and implant.

In instances where it is more practical to provide the histidine supplement parenterally, such formulations comprise, for example, sterile aqueous preparations of histidine which are preferably isotonic with the blood of the recipient. Suitable carrier solutions include phosphate buffered saline, saline, water, lactated ringers or dextrose (5% in water). Such formulations may conveniently be prepared by admixing histidine with water to produce a solution or suspension which is filled into a sterile container and sealed against bacterial contamination. Preferably, sterile materials are used under aseptic manufacturing conditions to avoid the need for terminal sterilization. Moreover, the foregoing parenteral formulations may optionally contain one or more additional ingredients among which may be mentioned preservatives (when the formulations are presented in multi-dose containers), buffers to provide a suitable pH value for the formulation, and sodium chloride, or glycerin, to render a formulation isotonic with the blood.

For I.V. administration, histidine may be used in free or salt form (for example, salts of alkali and alkaline earth metals such as sodium and calcium, respectively, salts if mineral acids such as HCl and sulfuric acid, or salts of organic acids, such as acetic acid. Amine addition salts may also be used in the practice of the invention, for example a phosphate amine addition salt. Examples of typical carriers are sterilized water, saline, and phosphate buffered saline. Optional additives include isotonic agents, stabilizers, pH controlling agents, agents necessary for the proper infusion of solutions, and water soluble dietary nutrients.

For oral administration, histidine is formulated with a pharmaceutically acceptable solid or liquid carrier. Solid form preparations include powders, tablets, pills, capsules, cachets, and dispersible granules. A solid carrier can be one or more substances which may also act as diluents, flavoring agents, solubilizers, lubricants, suspending agents, binders, preservatives, tablet disintegrating agents, or encapsulating materials. These may also include one or more excipients that is a selectively porous or slowly-dissolving layer-forming material or non-layer-forming material (e.g., polymeric materials) in order to render the oral dosage form sustained- or controlled-release.

For powder formulations, the carrier is a finely divided solid which is in admixture with the finely divided active component. For tablets, the active component is mixed in suitable proportions with the carrier having the necessary binding properties and compacted in the shape and size desired.

The powders, capsules and tablets preferably contain from five or ten to about seventy percent of histidine. Suitable carriers are magnesium carbonate, magnesium stearate, talc, sugar, lactose, pectin, dextrin, starch gelatin, tragacanth, methylcellulose, sodium carboxymethylcellulose, microcrystalline cellulose, a low melting wax, cocoa butter, and the like. The term "preparation" is intended to include the formulation of histidine with an encapsulating material as a carrier, thereby providing a capsule in which the amino acid component (with or without other carriers or excipients) is surrounded by a carrier. Similarly, cachets and lozenges are included. Tablets, powders, capsules, pills cachets, and lozenges can be used as solid dosage forms suitable for oral administration.

Another type of solid carrier useful in the practice of the invention is a foodstuff. Solid foodstuffs suitable for admixture with an effective daily supplementing amount of histidine are, for example, a cereal product, chewing gum, or a candy lozenge. For veterinary applications, histidine may be admixed directly into a grain ration of incorporated into a salt block. Likewise, histidine may be formulated with a liquid foodstuff, for example, milk, juices, liquid vitamin supplements, and oral rehydration(electrolyte) solutions (e.g., in those cases where dysmenorrhea causes diarrhea).

Liquid form preparations include solutions, suspensions, emulsions of histidine in, for example, of water, water/propylene glycol solutions, or other liquids, half-liquid bases, or optionally, in pharmaceutically acceptable solvents.

Also included are solid form preparations which are intended to be converted, shortly before use, to liquid form preparations for oral administration. These liquid forms include solutions, suspensions, and emulsions. These preparations may contain, in addition to a nutritionally beneficial amount of histidine, additives such as colorants, flavors, stabilizers, buffers, artificial and natural sweeteners, dispersants, thickeners, solubilizing agents, and the like.

The dietary supplement according to the invention is preferably in unit dosage form. In this way, the preparation is subdivided into unit doses containing appropriate quantities of the supplement. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

In another embodiment of the invention, a method for alleviating dysmenorrhea, pre-term labor or endometriosis encompasses co-administering a dietary histidine supplement with a separately formulated therapeutically active agent or compound (e.g., a drug, a hormone, or a bio-active molecule or macromolecule) to obtain an enhanced and/or more rapid relief of the condition sought to be alleviated. "Co-administration" within the context of this embodiment should be understood as meaning simultaneous or sequential administering of the dietary supplement and the therapeutic agent or drug, either by the same or different route of administration (e.g., oral histidine supplement and an intramuscular injection of a drug). However, "simultaneous" co-administration is not to be understood as conveying that the histidine supplement is within the same formulation as the therapeutically active drug or agent. The therapeutically active agents that are exemplified and enumerated below are known in the pharmaceutical art and accordingly, are separately formulated according to well-established, art-recognized practices.

Therapeutically active agents or compounds suitable for separate co-administration with histidine are those which are useful for abating or treating disorders such as dysmenorrhea and pre-term labor, agents for treating endometrial pain (e.g., NSAIDs, hormones), and agents for treating underlying reproductive disorders which as a result of correction or abatement cause dysmenorrhea. Examples of therapeutic agents for treating dysmenorrhea include, but are not limited to, tocolytic oxytocin antagonists (e.g., $\beta_2$-adrenergic agonists (ritodrine, terbutalin, and albuterol), magnesium sulfate, ethanol, amide substituted spiroindanylcamphorsulfonyl oxytocin antagonists, peptide oxytocin antagonists (e.g., as disclosed in U.S. Pat. No. 5,026,703) and spiro cyclic compounds such as spiro indene-piperidine disclosed e.g., in U.S. Pat. No. 5,670,509); nonsteroidal antiinflammatory drugs/prostaglandin synthetase inhibitors (e.g., aspirin, diflunisal, ibuprofen, indomethacin, clinoril, tolectin, zomepirac, naproxen, ketoprofen, suprofen, meclofenamate, meclofenamic acid, flufenamic acid, mefenamic acid, ketorolac, catallam, diclofenac sodium, phenylbutazone, p-chloromercuribenzoate and piroxicam); calcium supplements, pharmaceutically acceptable salts of calcium, and other pharmaceutically- recognized adminstrable forms of calcium; a heteropolycyclo-substituted heterocyclic amide thromboxane $A_2$ receptor antagonist (e.g., ifetroban or a pharmaceutically acceptable salt thereof); certain amidinoureas (e.g., those disclosed in U.S. Pat. No. 4,241,087), antiiflammatory arylmethylene and arylmethyl-indenoimidazoles (e.g., disclosed in U.S. Pat. No. 4,548, 943); and therapeutic peptides (e.g., U.S. Pat. No. 4,728, 640). Representative therapeutic agents for treating endometriosis include hormones, especially contraceptive regimens, danazol, and long-acting gonadotropin-releasing hormone analogues; therapeutic peptides (e.g., those disclosed in U.S. Pat. Nos. 4,728,640 and 4,743,589); and nonsteroidal antiinflammatory drugs, such as those recited previously. Representative therapeutic agents for managing pre-term or premature labor include certain NSAIDs (e.g., clinoril (Sulindac)), an activin antagonist (e.g., human follistatin, a polyclonal or monoclonal antibody or immunogenic fragment thereof capable of binding to activin, e.g., as described in U.S. Pat. No. 5,545,616); smooth muscle relaxant S-nitrosothiols; certain aromatase inhibitors (e.g., 4-hydroxy-4-androstene-3,17-dione or 4-acetoxy-4-androstene-3,17-dione); inhibitors of leukotriene biosynthesis, e.g.,aryl, hetero, polysubstituted indoles (e.g., as disclosed in U.S. Pat. Nos. 5,081,138 and 5,225,421); quinolin-2-ylmethoxy indoles, fluoro-substituted quinoline indoles, quinolin-2-ylmethoxy tetrahydrocarbazoles, tetrahydrocarbazole alkanoic acids, quinoline ether alkanoic acids, cycloalkyl(e.g., heptyl) indole alkanoic acids, indenyl hydroxamic acids, and hydroxy ureas. Many of these preterm labor therapeutics (e.g., the tocolytic oxytocin receptor antagonists, the heteropolycyclo indoles, the quinolyl indoles, the tetrahydrocarbazole alkanoic acids and the cycloalkyl indole alkanoic acids to name a few) are also useful for treating dysmenorrhea. Representative therapeutic agents for treating ovary dysfunction include hormone therapeutics and D-chiroinositol. The above listings are intended solely to be representative and non-limiting of the types of additional therapeutic agents that can advantageously be separately co-adminitered with a nutritionally supplementing amount of histidine. Other agents for treating female reproductive conditions or disorders and which are readily appreciated and/or routinely prescribed by a gynecologist/obstetrician are also intended and may be separately co-administered with a dietary supplement of histidine to obtain enhanced ameliorative effects.

EXAMPLES

The following examples are provided to illustrate, not limit, the scope of the invention.

CAPSULE FORM

A) A capsule (22 mm length, 8 mm dia) was filled with a mixture that was prepared by combining 20 g of L-histidine free base with 60 g of lactose. One capsule contained 20 mg of the active substance.

B) Similarly, a capsule was prepared containing 300 mg of L-histidine free base and 250 mg calcium carbonate by thoroughly admixing a proportionate amount of L-histidine, calcium carbonate, and sufficient lactose and filling a proportionate number of capsules of appropriate dimension to afford individual capsules having the above-specified dose of histidine and calcium supplements.

Histidine-containing soft gelatin capsules can be prepared as follows:

C) A mixture was formed by combining 500 mg of L-histidine free base with 10 mg of lecithin, 20 mg of beeswax and 420 mg of soybean oil. The mixture was encapsulated into a 16 mm oblong soft gelatin capsule. One capsule contains 500 mg of the active substance.

D) Similarly, a 250 mg dose of L-histidine was prepared by thoroughly admixing 250 mg of L-histidine free base with 5 mg of lecithin, 10 mg of beeswax, and 210 mg of soybean oil, and then encapsulated into a soft gelatin capsule of appropriate dimension.

TABLET FORM

A) 10 g of histidine were mixed with 60 g of lactose and 138 g of starch whereupon the mixture was wetted by a necessary amount of starch hydrogel. Two grams of magnesium stearate were added to the mixture after it was granulated and homogenized.

The mixture was then pressed to tablets. Each tablet was about 250 mg weight and 5 mm diameter and contained a 10 mg dose of the active substance.

B) Similarly, 500 mg tablets were prepared in which an amount of histidine corresponding to the 500 mg dose was added to proportionate amounts of lactose, starch hydrogel, and magnesium stearate, followed by granulating, homogenization, and pressing into tablets.

I.V. SOLUTION

A) A typical i.v. solution for practice of the invention can be prepared by dissolving a specified number of moles of histidine to obtain the desired supplement dose in sterilized water and stirring the solution to homogeneity. Acetic acid is added to the resulting aqueous solution of histidine to adjust the same to a pH of 7.0. The resulting aqueous solution is subjected to millipore filtration and charged under nitrogen gas into a vessel for an infusion solution. The product infusion solution was obtained by autoclaving under the usual conditions.

B) A combination supplement for i.v. administration comprised of calcium gluconate in an amount to deliver from about 2.0 mEq to about 15 mEq, and 10% L-histidine in a 5% dextrose solution, solubilized with lactic acid, and pH adjusted with HCl.

C) A combination supplement for i.v. administration in alleviating pre-term labor is comprised of magnesium sulfate in an amount sufficient to elevate the serum Mg level from about >2.5 mEq/L to about 7.5 mEq/L, and 10% L-histidine in a 5% dextrose solution, solubilized with lactic acid, and pH adjusted with HCl.

The invention now being fully described, it will be apparent to one of ordinary skill in the art that many changes and modifications can be made thereto without departing from the spirit or scope of the invention as set forth herein. It is therefore to be understood that within the scope of the appended claims, the invention may be practiced otherwise than as specifically described herein.

What we claim is:

1. A method for alleviating dysmenorrhea or at least one sequela thereof in a human female, said method comprising administering to said human female at a time prior to menses and continuing for the duration thereof, a dietary supplement of D-histidine, L-histidine, a therapeutically acceptable salt of histidine which can be reduced to D- or L-histidine, or mixtures thereof, in an amount that is effective to alleviate dysmenorrhea or at least one sequelae thereof.

2. The method according to claim 1 wherein said step of administering histidine comprises oral administration, intravenous injection or infusion, or combinations thereof.

3. The method according to claim 2 wherein said step of administering histidine is by oral administration.

4. The method according to claim 1 wherein said dietary supplement of histidine comprises from about 500 mg to 30 g of histidine daily.

5. The method according to claim 4 wherein said dietary supplement of histidine is administered as early as one week prior commencement of ovulation in a menstrual cycle.

6. The method according to claim 3 wherein said step of administering histidine comprises administering a controlled-release oral dosage form of histidine.

7. The method according to claim 1 wherein said dysmenorrhea is a primary or a secondary dysmenorrhea.

8. The method according to claim 7 wherein said dysmenorrhea to be alleviated is a secondary dysmenorrhea arising as a sequela of an underlying pathologic condition selected from the group consisting of endometriosis, pelvic inflammation, pelvic infection, adenomyosis, uterine myoma, uterine polyps, uterine adhesions, congenital malformations of the Mullerian system, cervical stenosis, ovarian cysts, pelvic congestion syndrome, and Allen-Master's syndrome.

9. The method according to claim 7 wherein said secondary dysmennorrhea to be alleviated is caused by intrauterine device use by said human female.

10. The method according to claim 1 further comprising co-administering a calcium supplement with histidine.

11. A method for alleviating pelvic pain in a human female as a result of endometriosis, comprising administering to said human female a dietary supplement of D-histidine, L-histidine, a therapeutically acceptable salt of histidine which can be reduced to D- or L-histidine, or mixtures thereof, in an amount that is effective to alleviate said pelvic pain.

12. The method according to claim 11 wherein said dietary supplement of histidine is from about 500 mg to 30 g of histidine daily.

13. The method according to claim 11 wherein said step of administering histidine comprises oral administration, intravenous injection or infusion, or combinations thereof.

14. The method according to claim 13 wherein said step of administering histidine comprises oral administration.

15. The method according to claim 14 wherein said step of administering histidine comprises administering a controlled-release oral dosage form of histidine.

16. The method according to claim 11 further comprising co-administering with said dietary supplement of histidine an additional dietary or nutritional supplement which is also useful for alleviating endometriosis and sequelae thereof.

17. The method according to claim 16 wherein said additional dietary or nutritional supplement comprises a mineral/electrolyte comprised of a magnesium salt or a calcium salt.

18. A method for alleviating pre-menstrual and menstrual cramping in a woman, comprising administering to said woman either before onset of menses or at commencement thereof, or both, a dietary supplement of D-histidine, L-histidine, a therapeutically acceptable salt of histidine which can be reduced to D- or L-histidine, or mixtures thereof, in an amount effective to alleviate pre-menstrual and menstrual cramping.

19. The method according to claim 18 wherein said step of administering said dietary supplement of histidine comprises oral administration, intravenous injection or infusion, or combinations thereof.

20. The method according to claim 19 wherein said dietary supplement of histidine is administered orally.

21. The method according to claim 20 wherein said step of administering histidine comprises administering a controlled-release oral dosage form of histidine.

22. The method according to claim 18 wherein said dietary supplement of histidine is from about 500 mg to 30 g of histidine daily.

23. The method according to claim 22 wherein said dietary supplement of histidine is administered as early as one week prior to commencement of ovulation in a menstrual cycle.

24. The method according to claim 22 wherein said dietary supplement of histidine is administered a) either as early as one week prior to a first day of menstruation or on first occurrence of menstrual cramps and b) continually administered for as many days of menses that menstrual cramps persist.

25. The method according to claim 18 further comprising co-administering with said dietary supplement of histidine an additional dietary or nutritional supplement which is useful in alleviating pre-menstrual and menstrual cramping.

26. A dietary supplement composition useful for alleviating or abating sequelae of female reproductive disorders comprising ovarian cysts, endometriosis, or dysmenorrhea, comprising A) an effective amount of D-histidine, L-histidine, a pharmacologically acceptable salt of histidine which can be reduced to D- or L-histidine, or mixtures thereof, B) an effective amount of calcium or pharmacologically acceptable salts thereof, and C) at least one pharmacologically acceptable carrier therefor.

* * * * *